United States Patent [19]
Campbell et al.

[11] Patent Number: 5,863,743
[45] Date of Patent: Jan. 26, 1999

[54] MEROSIN DEFICIENCY-TYPE CONGENITAL MUSCULAR DYSTROPHY

[75] Inventors: Kevin P. Campbell; Yoshihide Sunada, both of Iowa City, Iowa; Fernando M. S. Tomé, Paris; Michel Fardeau, Sceaux, both of France

[73] Assignee: University of Iowa Research Foundation, Iowa City, Iowa

[21] Appl. No.: 289,668

[22] Filed: Aug. 12, 1994

[51] Int. Cl.⁶ .................................................. G01N 33/53
[52] U.S. Cl. .......................... 435/7.21; 435/7.9; 435/960; 436/518; 436/811
[58] Field of Search .................................. 435/7.21, 7.9, 435/960; 436/63, 518, 811

[56] References Cited

U.S. PATENT DOCUMENTS 5,444,158  8/1995  Engvall et al. ......................... 530/395

FOREIGN PATENT DOCUMENTS

WO91/11462  8/1991  WIPO .

OTHER PUBLICATIONS

Tomé, F.M.S., et al., "Congenital muscular dystrophy with merosin deficiency", *C.R. Acad. Sci. Paris*, 317 : 351 (1994).
Sunada, Y., et al., "Deficiency of Merosin in Dystrophic*dy*Mice and Genetic Linkage of Laminin M Chain Gene to *dy*Locus", *The Journal of Biological Chemistry*, 269: 13729 (1994).
Toda, T., et al., "Localization of a gene for Fukuyama type congenital muscular dystrophy to chromosome 9q31–33", *Nature Genetics*, 5: 283 (1993).
Hayashi, Y. K., et al., "Abnormal localization of laminin subunits in muscular dystrophies", *J. of Neurological Sciences*, 119: 53 (1993).
Ehrig, K. et al., "Merosin, a tissue–specific basement membrane protein, is a laminin–like protein", *Proc. Natl. Acad. Sci*, 87: 3264 (1990).

*Primary Examiner*—Mary E. Mosher
*Assistant Examiner*—Donna C. Wortman
*Attorney, Agent, or Firm*—Kevin M. Farrell

[57] ABSTRACT

Disclosed is a method for aiding in the diagnosis of merosin deficiency-type congenital muscular dystrophy (CMD). The method is based on the discovery of a previously unidentified form of CMD which is characterized by a substantial reduction in the levels of merosin in skeletal muscle tissue containing normal levels of dystrophin and dystrophin-associated proteins.

6 Claims, 3 Drawing Sheets

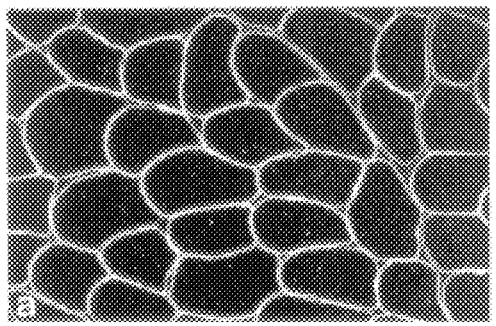
FIGURE IA
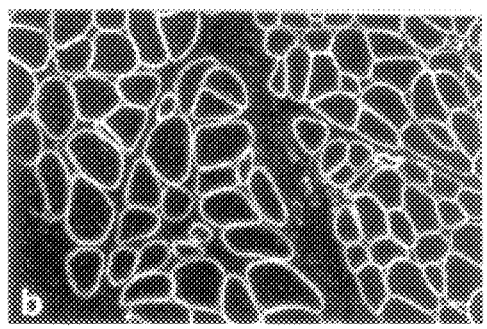
FIGURE IB
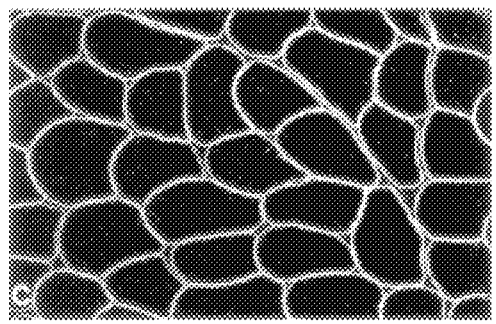
FIGURE IC
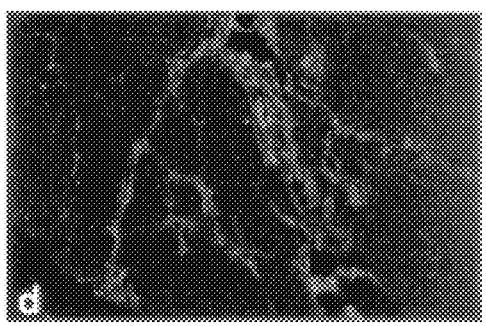
FIGURE ID
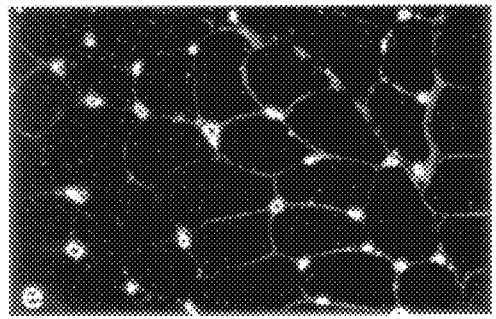
FIGURE IE
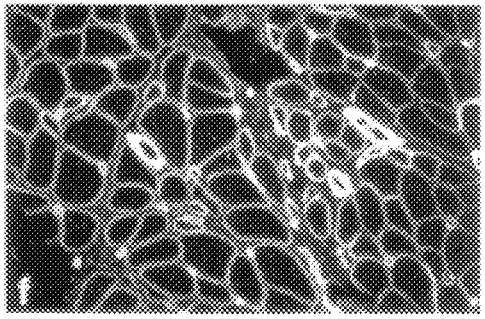
FIGURE IF

MEROSIN DEFICIENCY-TYPE CONGENITAL MUSCULAR DYSTROPHY

BACKGROUND OF THE INVENTION

Congenital muscular dystrophy (CMD), a very disabling muscle disease of early clinical onset, is the most frequent cause of severe neonatal hypotonia. Its manifestations are noticed at birth or in the first months of life and consist of muscle hypotonia, often associated with delayed motor milestones, severe and early contractures and joint deformities. Serum creatine kinase is raised, up to 30 times the normal values, in the early stage of the disease, and then rapidly decreases. The histological changes in the muscle biopsies consist of large variation in the size of muscle fibers, a few necrotic and regenerating fibers, marked increase in endomysial collagen tissue, and no specific ultrastructural features. The diagnosis of CMD has been based on the clinical picture and the morphological changes in the muscle biopsy, but it cannot be made with certainty, as other muscle disorders may present with similar clinico-pathological features.

Within the group of diseases classified as CMD, various forms have been individualized. The two more common forms are the occidental and the Japanese, the latter being associated with severe mental disturbances, and usually referred to as Fukuyama congenital muscular dystrophy (FCMD). The genetic lesion responsible for FCMD has recently been mapped to chromosome 9. It is unknown whether or not the rare cases of CMD associated with mental retardation or central nervous system abnormalities observed in occidental countries belong to the same disease entity. The determination of the gene (or genes) responsible for the various forms of CMD is required in order to clearly delineate specific members of the currently ill-defined genus.

BRIEF DESCRIPTION OF THE DRAWINGS

FIGS. 1a–j is a photographic representation showing immunocytochemical analysis of dystrophin (a and b), merosin (c and d), and laminins A (e and f) B1 (g and h) and B2 (i and j) in biopsied skeletal muscle. Shown is normal staining in a control, on the left (a, c, e, g and i) and the absence of merosin and overexpression of laminin A in a 2-year old female with CMD on the right (b, d, f, h, and j).

DETAILED DESCRIPTION OF THE INVENTION

Figure 1G:
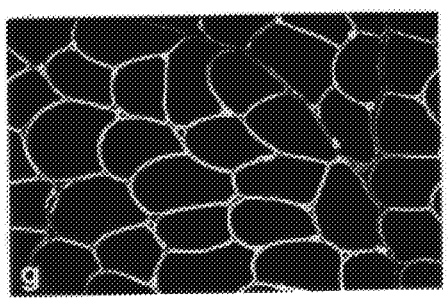
Figure 1H:
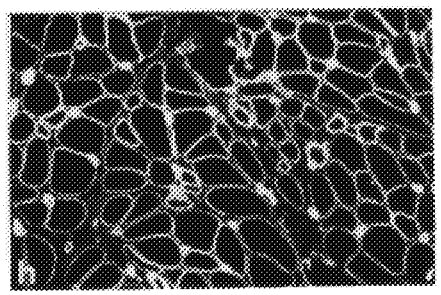
Figure 1I:
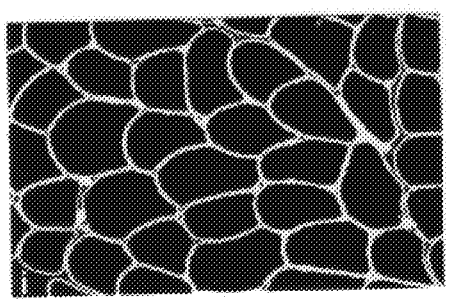
Figure 1J:
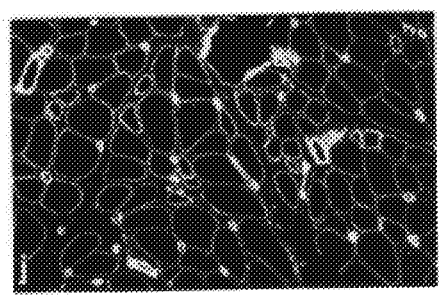

The present invention is based on the identification of a novel disease etiology which is responsible for a previously undefined member of the congenital muscular dystrophy family. The novel etiology, referred to herein as merosin deficiency-type congenital muscular dystrophy, was identified through the study of levels of specific proteins in mammalian muscle tissue.

Skeletal muscle dystrophin exists in a tightly associated oligomeric complex with dystrophin-associated proteins (DAPs); a 59-kDa intracellular dystrophin-associated protein triplet (59 DAP or syntrophin), three transmembrane dystrophin-associated glycoproteins of 35, 43, and 50-kDa (35 DAG, 43 DAG or β-dystroglycan, and 50 DAG or adhalin, respectively), a 25-kDa transmembrane dystrophin-associated protein, and a 156-kDa extracellular dystrophin-associated glycoprotein (156 DAG or a-dystroglycan). The primary structures of α and β-dystroglycan, and adhalin, and syntrophin have been determined by cDNA cloning. α-dystroglycan binds laminin or merosin, a major component of the basal lamina, and the NH2-terminal domain of dystrophin binds actin. These results indicate that the dystrophin-glycoprotein complex (DGC) links the subsarcolemmal actin cytoskeleton to the extracellular matrix.

The prototypical laminin molecule is a cross-shaped heterotrimer consisting of three types of chains, A (~400-kDa), B1 and B2 (~220-kDa). In recent years, various laminin isoforms with unique chain compositions have been identified in various tissues. In striated muscle and peripheral nerve, the tissue-specific laminin variant is merosin which is defined by having an M chain in place of an A chain. Merosin has diverse biological functions in mediating cell attachment and spreading and promoting neurite outgrowth, as well as forming the basal lamina meshwork with type IV collagen, fibronectin and heparan sulfate proteoglycan. Moreover, since the expression of merosin is developmentally regulated, merosin may play an important role in the maturation or differentiation of the neuromuscular system.

Muscle biopsies of patients with CMD are characterized by a marked increase in connective tissue. This observation has suggested that an abnormality of one of the components of the extracellular matrix could be involved in the pathogenesis of this disease. However, initial studies failed to detect specific changes in extracellular matrix proteins. As it was demonstrated that a large oligomeric complex of sarcolemmal glycoproteins associated with dystrophin provides a link between the subsarcolemmal cytoskeleton and laminin, experiments described below in Example 1 were designed to determine whether one of the laminin subunits could be involved in the classical non-Japanese form of the disease.

An anti-merosin antibody was selected for use in initial studies. In normal human skeletal muscle, immunocytochemical studies using an anti-merosin antibody show a uniform labeling around each muscle fiber. Example 1 describes the results of such labeling studies using skeletal muscle tissue from individuals afflicted with classical or occidental type congenital muscular dystrophy. Skeletal tissue from 13 patients who were diagnosed based on clinical observations as afflicted with occidental type congenital muscular dystrophy was analyzed using an anti-merosin antibody. In contrast to observations with normal skeletal muscle, immunocytochemical studies with tissue sections from these individuals showed no such uniform labeling around muscle fibers. The merosin deficiency in these individuals was confirmed by immunoblot analysis. Subsequent studies with other patients having indistinguishable clinico-pathological features of classical CMD, but from a geographically distinct region, do not present this deficiency. It was also determined that levels of dystrophin and dystrophin-associated proteins (i.e., 156 DAG, 59 DAP, 50 DAG, 43 DAG and 35 DAG) were approximately equivalent, as a percentage of total protein, to levels of dystrophin and dystrophin-associated proteins found in a normal (i.e., non-dystrophic) control muscle samples. These results are discussed in Example 1 which follows.

Further evidence of the role of merosin in the development of the CMD disease state is presented in Example 2. More specifically, experiments described in Example 2 demonstrate that merosin is a native ligand for α-dystroglycan (156 DAG), an extracellular component of the dystrophin-glycoprotein complex. In addition, a murine gene encoding one of three polypeptide chains which comprise merosin has been mapped to chromosome 10 close to the *dystrophia muscularis* (dy) locus (Sunada et al., (1994) *J. Biol. Chem.* 124: 381). The dy mutation is responsible for a severe neuromuscular disease resembling human muscular dystrophy.

Thus, in one aspect, the present invention relates to a method for aiding in the diagnosis of merosin deficiency-type congenital muscular dystrophy. This and other aspects of the invention are applicable to any mammalian muscle tissue, although human muscle tissue samples are preferred.

In the diagnostic method of the present invention, a muscle biopsy sample is obtained from an individual to be tested. Typically, an individual to be tested for merosin deficiency-type CMD is an individual exhibiting clinico-pathological features of classical CMD. These clinico-pathological features are described briefly above. Muscle samples are obtained from patients by surgical biopsy. The site of biopsy can be any skeletal muscle suspected of being dystrophic. Muscle groups about the shoulder and pelvic girdles, however, are the most affected and are likely to be the most common site of biopsy. Such muscle samples are analyzed by antibody staining to determine levels of dystrophin, dystrophin-associated proteins and merosin. The order of determination of these protein components is not critical and, under some circumstances, it may be possible to determine levels of dystrophin, dystrophin-associated proteins and merosin simultaneously. An otherwise identical set of antibody staining experiments is carried out, preferably in parallel, using normal (i.e., non-dystrophic) skeletal muscle tissue. Assuming that the levels of dystrophin and dystrophin-associated proteins are determined to be approximately equivalent, as a percentage of total protein, to levels of dystrophin and dystrophin-associated proteins found in the normal control muscle sample, a determination of substantial reduction in the extent of binding of the merosin-specific antibody to merosin is indicative of merosin deficiency-type congenital muscular dystrophy. To ensure that control and experimental extracts contain substantially similar quantities of protein, extracts are separated electrophoretically and stained, for example, with Coomassie blue. As used herein, substantial reduction in the extent of merosin-specific antibody binding refers to a level of reduction substantially equivalent to that obtained by the experimental procedure described in Example 1.

Methods for the determination of levels of dystrophin and dystrophin-associated proteins are carried out by conventional techniques. Such techniques are disclosed, for example, in U.S. Pat. Nos. 5,187,063; 5,260,209; and 5,308,752, the disclosures of which are incorporated herein by reference. International Publication Number WO 89/06286 also discloses such conventional techniques, as well as the nucleic sequence encoding dystrophin.

Briefly, antigen corresponding to dystrophin or dystrophin-associated proteins is isolated either from tissue which naturally expresses such protein, or by recombinant techniques using DNA sequences which have been demonstrated to encode either dystrophin or a component of the dystrophin-glycoprotein complex. Such proteins can be used to generate polyclonal or monoclonal antibodies which bind specifically to the antigen of interest.

The antibody can be used in connection with a conventional assay for the determination of levels of antigen in a tissue of interest, in this case, skeletal muscle tissue. Any method which enables the determination of protein levels present in skeletal muscle tissue based on antibody binding is useful in connection with the present invention. Preferred methods include Western blotting, immunocytochemical analysis and enzyme-linked immunoadsorbent assay (ELISA).

To determine levels of merosin in the skeletal muscle tissue sample, it is first necessary to generate antibody which is specifically reactive with merosin. Conventional techniques for the generation of monoclonal and polyclonal antibodies are used in connection with this aspect of the invention (see e.g., Antibodies: A Laboratory Manual; Harlow and Lane, eds., Cold Spring Harbor Laboratory, Cold Spring Harbor, New York (1988); Fardeau et al., (1993) *Acad. Sci. Paris* 316: 799–804; Engvall et al., (1990) *Cell. Regul.* 1: 731–40). The complete nucleic acid sequence encoding merosin has been reported (Vuolteenaho, et al. (1994) *J. Cell. Biol.* 124: 381). Therefore, antigen can be prepared using recombinant DNA methodologies in addition to more classical approaches. In addition, suitable antibodies are available from commercial sources as indicated in Example 1.

Antibodies specifically reactive with merosin can be used in any conventional assay for the determination of levels of antigen in a tissue of interest. As was discussed previously in connection with the determination of levels of dystrophin and dystrophin-associated proteins, such methods include, for example, Western blotting, immunocytochemical analysis and enzyme-linked immunoadsorbent assay (ELISA).

For assays which require solubilized extracellular matrix (e.g., ELISA and Western blotting), the amount of muscle obtained by biopsy should be sufficient to enable the extraction of merosin in a quantity sufficient for analysis. Preferably, the muscle tissue is homogenized by mechanical disruption using apparatus such as a hand operated or motor driven glass homogenizer, a Waring blade blender homogenizer, or an ultrasonic probe. Homogenization can be carried out, for example, in 20 volumes of EDTA-extraction buffer (10 mM EDTA, 50 mM Tris/HCl, pH 7.5, 150 mM NaCl, 1 mM PMSF, 0.75 mM benzamidine, 1 μg/ml aprotinin, 1 μg/ml of leupeptin, 1 μg/ml of pepstatin A) on ice for 2 hr. Following centrifugation, extracellular matrix solubilized in this manner can then be processed by conventional methods for use, for example, in Western blotting or ELISA analytical formats.

The solubilized extracellular matrix components, prepared as described above are analyzed by Western blotting by first separating the components on a 3–12% SDS polyacrylamide gel (Laemmli (1970) *Nature* 227, 680) followed by transfer to a solid support, such as a nitrocellulose membrane, forming an exact replica of the original protein separation but leaving the transferred proteins accessible for further study. This solid support bearing the transferred protein components is referred to as an immunoblot. The detection of transferred proteins can be accomplished by the use of general protein dyes such as Amido black or Coomassie brilliant blue. Antibodies which are specific for merosin can be labeled with a detectable reporter group and used to stain the protein transferred to the solid support. Alternatively, unlabeled antibodies specific for merosin are incubated with an immunoblot under conditions appropriate for binding. The specific binding of these antibodies to the muscle tissue sample is detected through the use of labeled secondary antibodies by conventional techniques.

The methods of the present invention can also be practiced in an enzyme-linked immunoadsorbent assay (ELISA) format. In this format, antibodies against merosin are adsorbed to a solid support, in most cases a polystyrene microtiter plate. After coating the support with antibody and washing, a solubilized sample is added. Merosin, if present, will bind to the adsorbed antibodies. Next, a conjugate that will also bind to the merosin is added. Conjugates are secondary antibody molecules to which an enzyme is covalently bound. After addition of a chromogenic substrate for the enzyme, the intensity of the colored reaction products generated will be proportional to the amount of conjugated enzyme and thus indirectly to the amount of bound merosin. Since the intensity of the developed color is proportional to the amount of merosin present, determination of the intensity of the color produced by a standard series of merosin concentrations will allow the calculation of the amount of merosin in an unknown sample. Many variations of this assay exist as described in Voller, A., Bidwell, D. E. and Bartlett, A., The Enzyme Linked Immunoadsorbent Assay (ELISA): A guide with abstracts of microplate applications, Dynatech Laboratories, Alexandria, Va. (1979).

Alternatively, tissue specimens (e.g., human biopsy samples) can be tested for the presence of the components of the dystrophin-glycoprotein complex by using monoclonal or polyclonal antibodies in an immunohistochemical technique, such as the immunoperoxidase staining procedure. In addition, immunofluorescent techniques can be used to examine human tissue specimens. In a typical protocol, slides containing cryostat sections of frozen, unfixed tissue biopsy samples are air-dried and then incubated with the anti-merosin antibody preparation in a humidified chamber at room temperature. The slides are layered with a preparation of fluorescently labeled antibody directed against the anti-merosin antibody. Labeled secondary antibodies are also useful for detection. The staining pattern and intensities within the sample are determined by fluorescent light microscopy.

By comparing the levels of merosin present in the tissue sample from the individual to be tested for merosin deficiency-type congenital muscular dystrophy with the levels observed in non-dystrophic control tissue treated in an otherwise identical manner, a substantial reduction in the level of merosin present can be determined. As shown experimentally in the Examples which follow, a substantial reduction in merosin levels correlates with merosin deficiency-type congenital muscular dystrophy.

EXAMPLE 1

In normal human skeletal muscle, immunocytochemical studies using an antibody against merosin (laminin M chain) show a uniform labeling around each muscle fiber (FIG. 1c). To determine whether tissue from individuals afflicted with classical or occidental type congenital muscular dystrophy exhibits a similar pattern, serial transverse sections (7 $\mu$m) of muscle fibers were immunostained with monoclonal antibodies against dystrophin (DYS2, Novocastra), merosin (M-chain) (Fardeau et al., (1993) Acad. Sci. Paris 316: 799–804; Engvall et al., (1990) Cell. Regul. 1: 731–40) (Chemicon), and the laminin subunits A(4C7) (Engvall et al., (1990) Cell. Regul. 1: 731–40), B1(4E10) (Engvall et al., (1986) J. Cell. Biol. 103:, 2457–2465), B2(2E80) (Engvall et al., (1986) J. Cell. Biol. 103:, 2457–2465)) (Gibco BRL).

Figure 2:
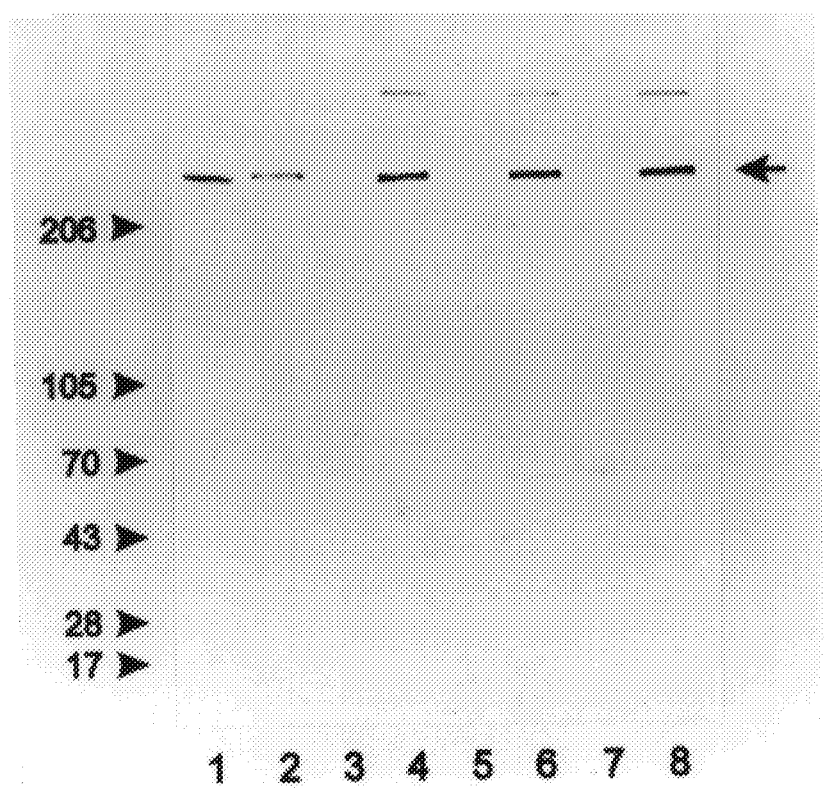
FIG. 2 is a photographic representation showing immunoblot analysis of EDTA-extracts from biopsied skeletal muscle specimens using a polyclonal antibody against merosin M chain. Lane 1: normal control; lanes 2, 4 and 6: children clinico-pathologically diagnosed as CMD (lane 2: 16-month-old female, lane 4: 4.5 year-old male; lane 6: 9-year-old female); lanes 3, 5 and 7: children with classical CMD and merosin-deficiency (lane 3: 10-month-old female, lane 5: 3-year old male, lane 7: 9-year old female); lane 8: 6-year-old male with Duchenne muscular dystrophy. The presence of a 300 kDa fragment of merosin M is indicated by the left-pointing arrow.
Figure 3A:
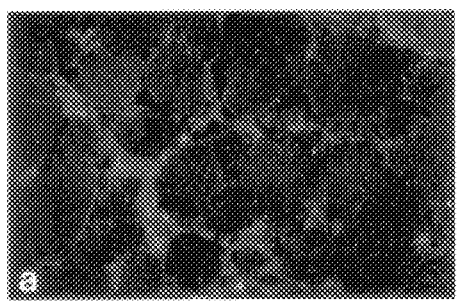
FIGS. 3a–h is a photographic representation showing immunocytochemical analysis of merosin in biopsied skeletal muscle. Merosin is absent in a 9-year-old male with CMD (a) and present in patients affected by other muscular dystrophies. Shown are a 6-year-old male with Duchenne (b), a 31-year old female with limb girdle linked to chromosome 15 (c), a 15-year-old female with severe childhood autosomal recessive with adhalin (50 kDa dystrophin associated glycoprotein) deficiency (d), a 34-year-old male with myotonic (e), a 75-year-old female with oculopharyngeal muscular dystrophies (f), a 9-year-old male with Ullrich syndrome (g); and a 6-year-old male clinico-pathologically diagnosed as CMD (h).
Figure 3B:
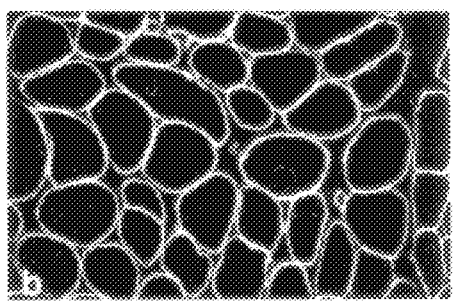
Figure 3C:
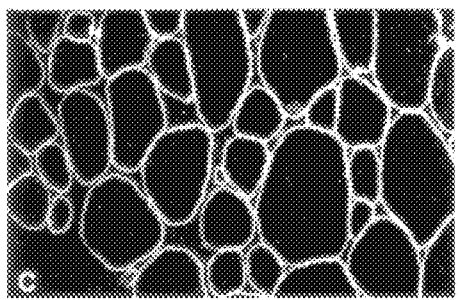
Figure 3D:
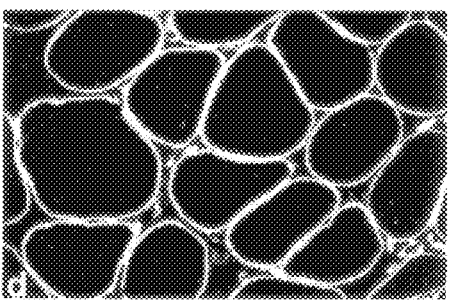
Figure 3E:
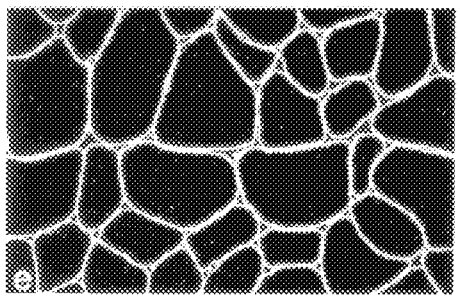
Figure 3F:
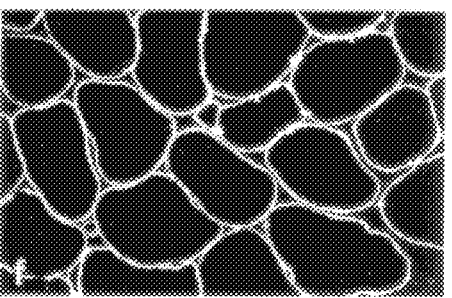
Figure 3G:
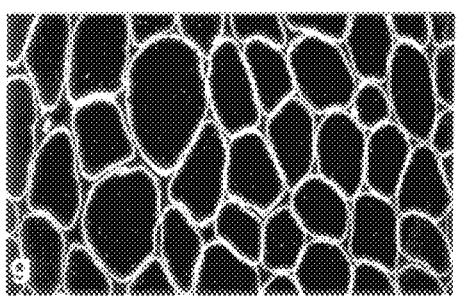
Figure 3H:
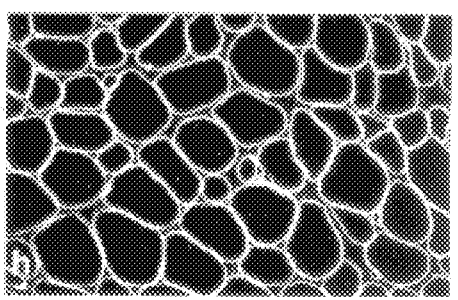

In contrast to the results from normal human skeletal tissue, there was no such labeling with the anti-merosin antibody in 13 patients (8 males and 5 females; mean age at muscle biopsy 2.46±0.69[SEM]) with a CMD of classical or occidental type (FIG. 1d). The merosin deficiency in these patients was confirmed by immunoblot analysis (FIG. 2). Cryosections (20 $\mu$m) from biopsied skeletal muscle were homogenized with 80 volumes of EDTA-extraction buffer (50 mM Tris-HCl, pH 7.5, 10 mM NaCl, 1 mM PMSF, 0.75 mM benzamidine, 1 $\mu$g/ml aprotinin, 1 $\mu$g/ml leucopeptin, 1 $\mu$g/ml pepstain A) and incubated in ice for 2 hours. After centrifugation, the protein concentration of each sample was determined. Samples containing 200 $\mu$g of protein were separated on 3–12% gradient SDS-PAGE in the presence of 1% 2-mercaptoethanol and transferred to nitrocellulose. The nitrocellulose transfer was stained with a rabbit polyclonal antibody against a recombinant mouse merosin M chain fragment. Immunocytochemical studies with antibodies against B1 and B2 laminin subunits showed labeling of the basal lamina similar to that seen in normal controls (FIG. 1g–j). The laminin A chain, which is weakly expressed in adult skeletal muscle (FIG. 1e), was overexpressed in most patients with merosin absence (FIG. 1f). In normal controls and patients with other muscular dystrophies (Duchenne, Becker, facioscapulohumeral, myotonic, oculopharyngeal, limb girdle linked to chromosome 15, severe childhood autosomal recessive with adhalin deficiency) the merosin (FIG. 3) as well as the other laminin subunits were normally expressed. No deficiency in merosin either by immunocytochemical (FIG. 3h) or by immunoblot analysis (FIG. 2) was found in seven children (2 males and 5 females; mean age at muscle biopsy 4.60±1.14[SEM]) with muscle disturbances and who, after exclusion of well-characterized muscle disorders, were considered, by the histopathological features of their muscle biopsies, as possibly belonging to the CMD group. It should be noted that, by immunocytochemistry, no abnormalities were seen either of dystrophin or the dystrophin-associated proteins in the thirteen patients in whom merosin was absent (FIG. 1b) as well as in the seven children with normal merosin.

This study shows that thirteen patients presenting with a classical picture of CMD have a specific deficiency in merosin. Other patients, who have indistinguishable clinicopathological features of classical CMD, do not present this deficiency. The lack of merosin allows, therefore, the precise identification of a particular form of CMD referred to herein as merosin deficiency-type congenital muscular dystrophy. Patients with diagnosis of CMD but having normal merosin must have a different form of CMD or other congenital muscle disorder. According to a mechanism common to Duchenne muscular dystrophy (DMD) and to severe childhood autosomal recessive muscular dystrophy with DMD-like phenotype (SCARMD), the absence of merosin apparently disrupts the link between the subsarcolemmal cytoskeleton and the extracellular matrix and lead to muscle fiber necrosis in CMD.

EXAMPLE 2

Merosin is the tissue-specific laminin isoform in the basal lamina of striated muscle and peripheral nerve, and consists of M, B1 or S, and B2 chains. In this Example, experiments are disclosed which demonstrate that merosin is a native ligand for α-dystroglycan, an extracellular component of the dystrophin-glycoprotein complex. In addition, the mouse M chain gene, Lama2, has been mapped close to the region of mouse chromosome 10 to which the *dystrophia muscularis* (dy) locus has been mapped. The dy mutation represents a severe neuromuscular disease resembling human muscular dystrophy. Analysis of merosin expression of dystrophic dy mice revealed a specific deficiency of merosin in skeletal muscle, cardiac muscle, and peripheral nerve. These results indicate that merosin deficiency is the primary defect which causes a type of congenital muscular dystrophy which is referred to herein as merosin deficiency-type congenital muscular dystrophy.

Experimental Procedures i) Nitrocellulose transfer overlays

Human placenta merosin (GIBCO BRL, Grand Island, N.Y.) was iodinated with [$^{125}$I]NaI using a lactoperoxidase/glucose oxidase reaction. A nitrocellulose transfer of a SDS-polyacrylamide gel containing purified DGC was overlaid with $^{125}$I-merosin as previously described (Ibraghimov-Beskrovnaya et al. (1992) *Nature* 355, 696–702).

ii) Immunoaffinity precipitation

Goat anti-mouse IgG-Sepharose was coupled with anti-adhalin monoclonal antibody IVD31. 70 μl of concentrated salt-free eluate of succinylated wheat germ agglutinin (sWGA)-agarose column chromatography from 1% digitonin-solubilized rabbit skeletal muscle membranes (Campbell and Kahl (1989) *Nature* 338, 259–262), which contains both DGC and merosin, was incubated with 100 μl of either immunoaffinity or control beads in the absence or presence of 10 mM EDTA overnight at 4° C. After centrifugation, proteins remaining in the supernatants were analyzed by 3–12% SDS-PAGE and immunoblotting.

iii) Immunofluorescence

Quadriceps muscle and sciatic nerve cryosections (7 μm) were immunostained with antibodies against laminin M chain, B1/B2 chain or type IV collagen as previously described (Ohlendieck et al., (1993) *Neurology* 43, 795–800).

iv) EDTA-extraction of merosin and immunoblotting

Freshly prepared cardiac muscle and sciatic nerve tissues or cryosections of skeletal muscle from age-matched control +/+ and dystrophic dy/dy mice were incubated with 20 volumes of EDTA-extraction buffer (10 mM EDTA, 50 mM Tris/HCl, pH 7.5, 150 mM NaCl, 1 mM PMSF, 0.75 mM benzamidine, 1 μg/ml aprotinin, 1 μg/ml of leupeptin, 1 μg/ml of pepstatin A) on ice for 2 hr. After centrifugation, samples containing 100 μg of protein were separated on 3–12% SDS-PAGE (Laemmli, U. K. (1970) *Nature* 227, 680–685) in the presence of 1% 2-mercaptoethanol and stained with Coomassie blue or transferred to nitrocellulose (Towbin et al., (1979) *Proc. Natl. Acad. Sci.* 76, 4350–4354). Nitrocellulose transfers were stained with a polyclonal antibody against mouse M chain as previously described (Ohlendieck et al., (1991) *J. Cell Biol.* 112, 135–148). For quantitative analysis, the immunoblots were labeled with $^{125}$I-labeled protein A (~250,000 cpm/ml; NEN, Boston, Mass.) and exposed to X-ray films. Densitometric scanning of autoradiograms was carried out on a computing densitometer (model 300S; Molecular Dynamics, Sunnyvale, Calif.) and analyzed using Image Quant (Molecular Dynamics) software.

v) Animals and Antibodies

129/ReJ and C57BL/6J strain dystrophic dy/dy mice (6–8 weeks) and age-matched normal control +/+ mice were obtained from Jackson Laboratory, Bar Harbor, Me. Polyclonal antibodies specific for each dystrophin-associated protein were affinity purified from sheep antiserum against the DGC as previously described (Ohlendieck and Campbell, (1991) *J. Cell Biol.* 115, 1685–1694; and Ibraghimov-Beskrovnaya et al. (1992) *Nature* 355, 696–702). The preparation and characterization of monoclonal antibodies IIH6 and IVD31, specific for α-dystroglycan and adhalin, respectively, have been previously described (Ervasti et al., (1990) *Nature* 345, 315–319; and Ervasti and Campbell, (1991) *Cell* 66, 1121–1131). A rabbit polyclonal antibody was raised against a recombinant human M chain fragment and its IgG fraction was used for immunoblotting. Since sheep anti-DGC serum also recognized merosin, a polyclonal antibody specific for a 300-kDa fragment of M chain was affinity-purified using purified human placenta merosin. Rabbit polyclonal antibodies specific for mouse laminin B1/B2 chain or mouse type IV collagen were obtained from Upstate Biotechnology Inc., Lake Placid, N.Y. or Biodesign International, Kennebunkport, Me., respectively.

Results

During the process of DGC purification described previously (Ervasti et al. (1991) *J. Biol. Chem.* 266, 9161–9165), the majority of merosin is removed by washing membranes with 0.6M KCl. However, residual merosin was coeluted with DGC from an sWGA-agarose column under salt-free conditions, and cosedimentated with DGC on a 5–30% sucrose density gradient. In addition, sheep anti-DGC serum recognized merosin, but not laminin A chain. $^{125}$I-merosin overlay demonstrated that merosin binds α-dystroglycan following transfer to a nitrocellulose membrane. To confirm the binding of merosin to α-dystroglycan, immunoadsorption experiments of salt-free sWGA eluate from solubilized rabbit muscle membranes were performed using anti-adhalin immunoaffinity beads. Immunoblot analysis of proteins in the supernatants revealed that anti-adhalin beads precipitated merosin as well as dystrophin and all DAPs in the absence of EDTA. In the presence of 10 mM EDTA, dystrophin and all DAPs were also precipitated, although less effectively. However, precipitation of merosin was completely abolished, indicating that the binding of merosin to α-dystroglycan was inhibited by addition of 10 mM EDTA. Although it has been previously shown that α-dystroglycan is a non-integrin laminin receptor (Ibraghimov-Beskrovnaya et al. (1992) *Nature* 355, 696–702; and Ervasti and Campbell, (1993) *J. Cell Biol.* 122, 809–823), these results demonstrated that merosin is a native ligand of α-dystroglycan in skeletal muscle.

The M chain genomic DNA probe, pgmm4-3, identified BamHI fragments of 18.8 kb in NFS/N and C58/J and 15.0 kb in *M. spretus*. Analysis of the parental mice of the M. m. musculus cross failed to identify polymorphic fragments using this probe following digestion with 13 different enzymes. Analysis of the progeny of the *M. spretus* cross for inheritance of Lamm, the gene for the M chain, demonstrated that this locus was linked to markers on proximal mouse Chr 10 and positioned Lamm just distal to Myb.

The data indicate that the Lamm gene maps to a region of mouse Chr 10 which shows conserved linkage to human chromosome 6 q, which is consistent with a map location for the human homolog of this gene (Vuolteenaho et al. (1994) *J. Cell Biol.* 24, 381–394). The map location of Lamm in the mouse places this gene in the same region of the genome known to contain the gene dy. Although composite genetic maps position dy proximal to Myb (Hillyard et al. (1993) *Mouse Genome* 91, 15–39; and Taylor et al. (1993) *Mamm. Genome* 4, s154–s163), dy and Myb have never been mapped relative to one another, and furthermore, dy had not been mapped relative to any other molecular markers. Thus, the mapping data of Lamm disclosed herein supports the conclusion that a mutation in this sequence is responsible for the dy phenotype. This observation led to an examination of the status of merosin expression in dystrophic dy mice.

Immunofluorescence analysis of merosin and type IV collagen, another component of the basal lamina, in control +/+ and dy/dy skeletal muscle and sciatic nerve was carried out. More specifically, seven μm-thick transverse cryosections of the quadriceps skeletal muscle (skeletal) and sciatic nerve (nerve) from 7-week-old 129/ReJ strain +/+ (control) and 7-week-old 129/ReJ strain dystrophic dy/dy (dy/dy) mice were labeled by indirect immunofluorescence with affinity-purified antibodies against a 300-kDa fragment of M chain (M chain) or polyclonal antibody against B1/B2 chain (B1/B2 chain) or type IV collagen (collagen IV).

In control skeletal muscle, M chain, B1/B2 chain and type IV collagen were localized throughout the basal lamina surrounding the sarcolemma. In dy/dy skeletal muscle, the immunostaining intensity of M chain was significantly decreased, whereas the immunostaining of B1/B2 chain and type IV collagen was indistinguishable between control and dy/dy skeletal muscle. Laminin M chain was localized to the endoneurial basal lamina surrounding Schwann cells in control nerve. In dy/dy nerve, M chain immunostaining was very faint, although the immunostaining of B1/B2 chain and type IV collagen in the endoneurial basal lamina and the perineurium was similar to that in control nerve.

EDTA-extracts from skeletal muscle, cardiac muscle and sciatic nerve were separated by SDS-PAGE. Coomassie blue staining of the gel revealed that the overall protein composition in each sample was similar between control and dy/dy mice. M chain polypeptide migrates as two fragments of 300-kDa and 80-kDa under reducing conditions (Ehrig et al. (1990) *Proc. Natl. Acad. Sci.* 87, 3264–3268). A rabbit polyclonal anti-M chain antibody detected a COOH-terminal 300-kDa fragment of M chain and a 600-kDa component. The latter consists of a 300-kDa M chain fragment and B1 and/or B2 chains as determined by immunoblot analysis. However, the relative abundance of a 300-kDa fragment and a 600-kDa component was significantly reduced in dy/dy skeletal muscle, cardiac muscle, and peripheral nerve. The reduction of merosin in dy/dy mice was quantitated using $^{125}$I-protein A-labeled immunoblots. Densitometric scanning of autoradiographs revealed a 94% reduction in skeletal muscle, a 96% reduction in cardiac muscle, and a 97% reduction in peripheral nerve when compared with age-matched control mice. Taken together with the gene mapping data, these results support the conclusion that an M chain gene mutation is the cause of the dy phenotype. The size of a 300-kDa fragment of M chain detectable in dy/dy mice was indistinguishable from that in control +/+ mice and the merosin whole molecule of 700-kDa was detected under non-reducing conditions in dy mice, suggesting that a large deletion in the M chain gene is unlikely.

Dy mice present severe dystrophic muscle pathology which mimics human muscular dystrophy like DMD. In DMD patients (Ervasti et al., (1990) *Nature* 345, 315–319; Ibraghimov-Beskrovnaya et al. (1992) *Nature* 355, 696–702; and Ohlendieck et al., (1993) *Neurolgy* 43, 795–800) and mdx mice (Ohlendieck and Campbell, (1991) *J. Cell Biol.* 115, 1685–1694), the absence of dystrophin leads to a drastic reduction of all DAPs. In severe childhood autosomal recessive muscular dystrophy with DMD-like phenotype, a specific deficiency of adhalin was identified (Matsumura et al. (1992) *Nature* 359, 320–322; Fardeau et al. (1993) *C. R. Acad. Sci. Paris* 316, 799–804; and Passos-Bueno et al., (1993) *Hum. Molec. Genet.* 2, 1945–1947). Thus, disruption of a linkage between the subsarcolemmal cytoskeleton and the extracellular matrix caused by the deficiency of DGC component(s) plays a crucial role in the pathogenesis of these muscular dystrophies. However, previous study demonstrated that all components of the DGC appear normal in dy mice (Ohlendieck and Campbell, (1991) *J. Cell Biol.* 115, 1685–1694). Since merosin is a native ligand for α-dystroglycan in skeletal muscle, the deficiency of merosin results in disruption of this critical link leading to muscle cell necrosis.

We claim:

1. A method for aiding in the diagnosis of a merosin deficiency-type congenital muscular dystrophy, which is not Fukuyama congenital muscular dystrophy, in an individual comprising the steps of:

a) providing an experimental muscle tissue sample from the individual, treated if necessary to render components available for antibody binding, the experimental muscle tissue sample being characterized by levels of dystrophin and dystrophin-associated proteins which are approximately equivalent, as a percentage of total protein, to levels of dystrophin and dystrophin-associated proteins found in a normal control muscle sample from an individual who is not afflicted with muscular dystrophy;

b) contacting the experimental muscle tissue sample with an antibody which binds to merosin, under conditions appropriate for binding;

c) detecting the extent of binding of the antibody to merosin in the experimental muscle tissue sample; and d) comparing the extent of binding of the antibody to merosin in the experimental muscle tissue sample, to the extent of binding of the antibody to merosin in a normal control muscle tissue, a substantial reduction in the extent of binding to the experimental muscle tissue, as compared to control tissue, being indicative of a merosin deficiency-type muscular dystrophy which is not Fukuyama congenital muscular dystrophy.

2. The method of claim 1 wherein the experimental muscle tissue sample is skeletal muscle tissue.

3. A method for aiding in the diagnosis of a merosin deficiency-type congenital muscular dystrophy, which is not Fukuyama congenital muscular dystrophy, in an individual comprising the steps of:

a) providing an experimental muscle tissue sample from the individual which is characterized by levels of dystrophin and dystrophin-associated proteins which are approximately equivalent, as a percentage of total protein, to levels of dystrophin and dystrophin-associated proteins found in a normal control muscle sample from an individual who is not afflicted with muscular dystrophy;

b) solubilizing the experimental muscle tissue sample;

c) separating the components of the experimental muscle tissue sample by electrophoresis;

d) transferring the separated components from step c) to a solid support to form an immunoblot;

e) contacting the immunoblot with an antibody specific for merosin under conditions appropriate for the binding of the antibody to merosin, if present;

f) removing non-specifically bound material;

g) detecting specific binding of the antibody to merosin;

h) comparing the extent of antibody binding to the immunoblot prepared from the solubilized experimental muscle tissue sample to the extent of antibody binding to an otherwise identical immunoblot prepared from normal control muscle tissue, a substantial decrease in the extent of antibody binding to the immunoblot prepared from the experimental muscle tissue sample being indicative of a merosin deficiency-type congenital muscular dystrophy which is not Fukuyama congenital muscular dystrophy.

4. The method of claim 3 wherein the experimental muscle tissue sample is a skeletal muscle tissue sample.

5. A method for aiding in the diagnosis of a merosin deficiency-type congenital muscular dystrophy, which is not Fukuyama congenital muscular dystrophy, in an individual comprising the steps of:

a) providing an experimental histological muscle or nerve tissue section from the individual, wherein the tissue section is characterized by levels of dystrophin and dystrophin-associated proteins which are approximately equivalent, as a percentage of total protein, to levels of dystrophin and dystrophin-associated proteins found in a normal control tissue section from an individual who is not afflicted with muscular dystrophy;

b) contacting the experimental histological muscle or nerve tissue section with an antibody specific for merosin under conditions appropriate for the binding of the antibody to merosin;

c) removing non-specifically bound antibody;

d) detecting specific binding of the antibody to merosin; and e) comparing the extent of antibody binding to the experimental histological muscle or nerve tissue section to the extent of antibody binding to an otherwise identical histological muscle or nerve tissue section from normal control tissue, a substantial decrease in the extent of antibody binding to the experimental histological muscle or nerve tissue section being indicative of a merosin deficiency-type congenital muscular dystrophy which is not Fukuyama congenital muscular dystrophy.

6. The method of claim 5 wherein the experimental histological muscle or nerve tissue section is a skeletal muscle tissue section.

* * * * *